US006955826B2

(12) United States Patent
Lamb et al.

(10) Patent No.: US 6,955,826 B2
(45) Date of Patent: Oct. 18, 2005

(54) PROCESS FOR THE PROVISION OF A PLANT EXTRACT CONTAINING CONDENSED TANNINS, WITH ASTRINGENT CHARACTERISTICS, MODIFIED BY COPOLYMERIZATION, FOR USE IN TANNING AND RETAINNING OF SKINS, A PLANT EXTRACT WITH ASTRINGENT CHARACTERISTICS, MODIFIED BY COPOLYMERIZATION, AND USE OF A MODIFIED PLANT EXTRACT CONTAINING TANNINGS

(75) Inventors: Luiz Henrique Lamb, Triunfo (BR); Otavio Decusati, Montenegro (BR)

(73) Assignee: Tanac S.A., Montenegro RS (BR)

( * ) Notice: Subject to any disclaimer, the term of this patent is extended or adjusted under 35 U.S.C. 154(b) by 43 days.

(21) Appl. No.: 10/446,109

(22) Filed: May 28, 2003

(65) Prior Publication Data

US 2004/0137093 A1 Jul. 15, 2004

(30) Foreign Application Priority Data

Jan. 13, 2003 (BR) ............................................ 0300037

(51) Int. Cl.[7] ................................................ A61K 35/78
(52) U.S. Cl. ...................................................... 424/725
(58) Field of Search .......................................... 424/725

(56) References Cited

U.S. PATENT DOCUMENTS 4,579,927 A * 4/1986 Patel et al. ................. 527/400

* cited by examiner

*Primary Examiner*—Susan Coe
*Assistant Examiner*—Susan B. McCormick-Ewoldt
(74) *Attorney, Agent, or Firm*—Birch, Stewart, Kolasch & Birch, LLP

(57) ABSTRACT

A process for obtaining a plant extract containing condensed tannins, with astringent characteristics, and modified by copolymerization, produces a material suitable for the tanning and retanning of skins. The process includes adding water to a reactor, adding a copolymerization agent, adding thioglycolic acid and allowing to react, adjusting pH, mixing a powdered extract of a plant or tannin to a desired concentration, raising the temperature, adding sodium bisulfite, and keeping the reaction heated and at pressure for about 4 hours.

22 Claims, No Drawings

PROCESS FOR THE PROVISION OF A PLANT EXTRACT CONTAINING CONDENSED TANNINS, WITH ASTRINGENT CHARACTERISTICS, MODIFIED BY COPOLYMERIZATION, FOR USE IN TANNING AND RETAINNING OF SKINS, A PLANT EXTRACT WITH ASTRINGENT CHARACTERISTICS, MODIFIED BY COPOLYMERIZATION, AND USE OF A MODIFIED PLANT EXTRACT CONTAINING TANNINGS

FIELD OF THE INVENTION

The present invention refers to a process for altering the elementary molecule of the condensed tannin obtained from Mimosa, increasing the average molecular weight thereof by selecting the raw material and controlling the extraction process to provide a selectivity of the tanning agents, with the addition of sulphite radicals to the tannin molecule to provide an increase in solubility and the consequent penetration of the extract into the skin, and the reaction with thermoplastic resins for adequation of the molecular weight and other characteristics that are extrinsic to acrylic resins.

BACKGROUND OF THE PRESENT INVENTION AND PRIOR ART

The process of transformation of hides into leather is one of the oldest human activities, existing since prehistoric times, when the hides were used as clothing for protection against the cold.

The first tannage, which is the process for transforming the hide, a putrescible material, in leather, a material that is stable and resistant to microorganisms, probably happened by chance. Some hides may have been placed in contact with tannin-rich plants, and the tanning may have been caused thereby through the action of rainfall.

In the present days, the hide tanning industry uses advanced technologies, thereby allowing to achieve a high level of productivity. To this end, among other aspects, there contribute the so called tanning agents, which are substances of plant, mineral or synthetic origin that will interact with the collagen fibers of the hide, thereby promoting the tanning thereof.

There should be pointed out the mineral agents, such as chrome salts, and particularly chrome sulfate. The synthetic agents are basically comprised by naphthalene sulphonic acids or salts and compounds derived from carbolic acid. In the category of tanning agents obtained from plants, a great variety of plants evidence the presence of substances with tanning properties.

The presence of tanning substances occurs in practically every plant in the vegetable kingdom, and especially in the superior plants. The localization of the tannin in the plants is equally varied, as it may be present in the trunk, the leaves, the bark and the roots. The occurrence thereof takes place in isolated cells or in cell groups, or yet in special cavities of the plant, and it commonly occurs in the cytoplasm of the plant cells.

The various plant extracts provide to the final products of tannage of hides, the tanned leathers, various characteristics according to the plant wherefrom the plant extracts were obtained.

However, the amount of plant species which are economically feasible to exploit is very restricted, and depending on the species the amounts of tannins present therein, as well as the characteristics of such tannins and the conditions related to the plant exploitation itself, may exhibit variation.

Among the main species there are included the Acacia Mimosa (*Acacia mearnsii* de Wild), the Quebracho (*Schinopsi lorentzi*), the Chestnut (*Castanea Vesca*), zumagre, gambir among others. Of these, only the Acacia Mimosa has a production system exclusively based on plants obtained by reforesting methods.

Chemically, the tannins are classified in two groups, according to their chemical structure: (i) the condensed tannins and (ii) the hydrolyzable tannins.

The hydrolyzable or pyrogallic tannins are polyester structures easily hydrolyzable by the action of strong acids or yet of enzymes. As a result of this hydrolysis there are obtained sugars, alcohols and phenol carboxylic acid. The phenol carboxylic acid will dissociate into gallic acid and ellagic acid. The extracts of Chestnut constitute typical examples of hydrolyzable or pyrogallic tannins.

The tannins classified as condensed tannins are also called catecholic tannins or phlobatannins. They are comprised of flavonoid units of the type flavan 3,4-diol and flavan 3-ol, with various degrees of polymerization therebetween. When treated with strong acids under heat, they start a progressive polymerization process, up to complete polymerization, originating amorphous tannins, known as phlobaphenes. The extracts of Acacia Mimosa are characteristic examples of catecholic type tannins or phlobatannins.

The extracts of Acacia Mimosa, which are of the catecholic tannin or phlobatannin types, are comprised of flavonoid units of the type flavan 3,4-diol and flavan 3-ol, with various degrees of cross-polymerization. The chemical binding between the tannin of this group and the collagen fibers occurs by interactions of the hydrogen binding type, between the phenolic hydroxylic groups and certain groups associated to the polypeptidic chain. Those extracts of the catecholic tannin or phlobatannin types evidence fast penetration into the hide, good dispersion among the collagen fibers, high resistance to electrolytes, a tanning rate of about 70 to 74%, a rate of non-tanning fraction of about 20 to 25%, an astringency of about 3.5 (ratio of tanning agents to non-tanning matter).and a pH value of about 4.8 to 5.2.

The extracts of Quebracho are of the condensed type and the maturation of this species is completed at the age of 80 years, whereupon the yield in tannin is particularly advantageous. Those extracts exhibit a high content of non-soluble matter and a high astringency (ratio of tanning agents to non-tanning matter).

The process of chemical modification of the extracts of Acacia Mimosa has carried out for many years, using sulphites and bisulphites usually in the form of sodium salts, for the purpose of altering the solubility of the extracts and particularly the color of these extracts.

Regarding past developments, the present inventors may cite as prior art examples the following papers: Belavsky, E.—O Curtume no Brasil (*Tannage in Brazil*)—Porto Alegre, Editora Globo, 1965; Bienkiewica, K—Physical Chemistry of Leather Making—Robert E. Krieger Publishing Co., Inc.—USA, 1993; Hoinacki, E.—Peles e Couros (*Skins and Hides*)—$2^a$ Ediç̃ao ($2^{nd}$ *Edition*) SENAI/RGS—Porto Alegre, 1989; Howes, F. N.—Vegetable Tanning Materials, London, Butterworths Scientific Publications, 1953; Leather Industries Research Institute—Wattle Tannin and Mimosa Extract—Grahamstown, South Africa, 1955; Mugica, M. G. & Ochoa, J. T. Los Taninos Vegetales (*Plant-Derived Tannins*), Madrid, Instituto Florestal de Investigaciones Y Experiencias, 1969; O'Flaherty, F.; Reddy, W. T.; Lollar R. M.—The Chemistry and Technology of Leather—Vol. IV—Evaluation of Leather—Reinhold Publishing Corporation, New York, 1965; Pizzi, A.—Wood Adhesives—Chemistry and Technology—Marcel Becker, Inc.—New York, 1983; Sherry, S. P.—The Black Wattle—University of Natal Press—South Africa, 1971; TEPF—Tanning Extract Producers Federation—A Survey of Modern Vegetable Tannage—England, 1974.

According to Pizzi, in Wood Adhesives—Chemistry and Technology—1983, the sulphitation of the tannin present in the extracts is one of the oldest and most widely used reactions in flavonoid chemistry. As a rule, the sulphitation provides to the tannins a decrease in viscosity and an increase in solubility. Both these effects are due to the following factors:

1. The elimination of the heterocyclic ether group, which is water-repellent, and as known by the specialists the aqueous extracts of tannin are not actual solutions but rather hydrocolloidal suspensions, wherein a part of the tannin molecule maintains the tannin solubilized while the other part tends to separate the tannin from the solution.

2. The introduction of the sulphonic group and one other hydroxyl group, both hydrophilic.

3. Decrease in the rigidity of the polymer, an esteric restriction, and the intermolecular hydrogen bonding resulting from the opening of the heterocyclic ring.

4. The acid hydrolysis of the hydrocolloidal starches and the interflavonoid bonds.

The following is a typical reaction in the process according to the present invention:

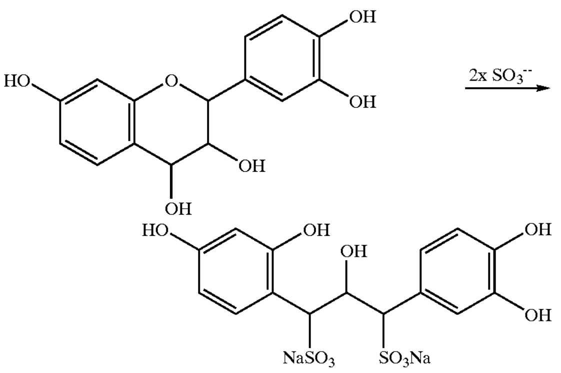

The Present Invention

The present invention refers to a process for industrial-scale manufacture of a plant extract containing condensed tannins of the catecholic tannin or phlobatannin types, obtained by means of aqueous lixiviation (leaching) of the bark of Acacia Negra, and chemical modification thereof for the purpose of using the same to act in the process of tanning or retanning of skins, maintaining the characteristics of the extract of Acacia Mimosa and particularly enhancing the characteristics that contribute to improve the retanning process.

In order to obtain the desired characteristics, there is promoted an alteration in the elementary molecule of the condensed tannin obtained from Acacia Mimosa, for the purpose of increasing the average molecular weight thereof. By selecting the raw material and controlling the extraction process, there is allowed a selectivity of the tanning agents, whereupon there is performed the addition of the sulphite radicals to the tannin molecule to increase the solubility thereof and consequently the penetration of the extract into the skin.

The reaction with thermoplastic resins prepared by polymerization of acrylic acid ($C_3H_4O_2$) or metacrylic acid ($C_4H_6O_2$), mixtures of acrylic acid and metacrylic acid or esters thereof occurs in order to be provided thereby an adequation of the molecular weight and other characteristics intrinsic to the acrylic resins.

The astringency of the product, which is measured by the ratio of tanning agent to non-tanning matter, is altered by means of an acid hydrolisis process, under controlled temperature and pressure, whereby a part of the phenolic fraction of the non-tanning matter will condense into larger units, in values between 3 and 9, being converted into a tanning fraction, and thereby in absolute terms, there is obtained an increase in astringency, of up to 4.5. The molecular weight of the final product is balanced to be kept within the desired range. This is achieved by controlling the raw material at the source forests of Acacia Mimosa, the reaction process and the reactions that take place in the raw material (the bark of Acacia Mimosa).

More specifically, the present invention comprises a process to obtain a plant extract containing condensed tannins of the catecholic tannin or phlobatannin types, such as, for example, those extracted from Acacia Mimosa, that is chemically modified with the purpose of imparting thereto characteristics that contribute to improve the use thereof in processes of tanning of skins and retanning of leathers.

The present process comprises the following steps:

(a) adding water to a reactor at a ratio between 2.0 and 5.8%, by weight, to the total load desired, according to the capacity of the reactor, preferably in a proportion of 3.7%;

(b) adding 1.2 to 2.5%, by weight, of glacial acrylic acid, preferably 1.6%, by weight, while stirring the mixture;

(c) adding thioglycolic acid at a ratio between 0.1 and 1.7%, by weight, preferably 0.6%, while cooling the mixture, whereupon there occurs the exothermal reaction and the temperature reaches 95° C., and after the reaction the product obtained thereby should be left to cool;

(d) adjusting the pH to a value in the range between 3.5 and 7.0, preferably to 6.0, by adding an alkali to the mixture;

(e) mixing a powdered extract of Acacia Negra with water at a ratio of about 0.5 to 2.0 kg per liter of water, preferably at a ratio of 1.0 to 1.5 kg per liter, and most preferably of 1.05 to 1.06 kg per liter; or optionally, using a solution of tannin in liquid form in a concentration of 25% to 60%, preferably in a concentration of 45% to 55%, and most preferably in a concentration of 50% of total solids content;

(f) raising the temperature of the mixture to a range between 67 and 98° C., and preferably to 84° C. to carry out the reaction, for a period of 2 to 7 hours, preferably for 5 hours;

(g) adding the sodium bisulphite at a ratio of 0.5 to 4.0%, by weight, preferably 1.8%, by weight, of bisulphite to the amount of tannin;

(h) raising the temperature of the mixture, keeping the same heated between 45 and 127° C., and preferably at 95° C., the pressure being comprised between 0.2 and 7 kgf/cm$^2$; and (i) allow a reaction time of about 4 hours.

Objects and Variations of the Process According to the Present Invention

One object of the present invention consists in providing a process to obtain modified tannins of the catecholic type, obtained by aqueous lixiviation (leaching) of the bark of Acacia Negra, chemically modified to act in the process of tanning or retanning of hides, maintaining the characteristics of the extract of Acacia Mimosa, however enhancing characteristics allowing to improve the retanning process.

In order to obtain the desired characteristics, there is promoted an alteration in the elementary molecule of the condensed tannin extracted from Acacia Mimosa, increasing its average molecular weight to a value between 1000 and 4000. By selecting the raw material and controlling the extraction process there is achieved a selectivity of the tanning agents, and thereupon there are added sulphite radicals to the tannin molecule to provide increased solubility and consequent penetration of the extract into the skin.

The process according to the present invention allows to produce a modified plant extract of Acacia Mimosa, Acacia Negra, having astringent and superior characteristics. In the process according to the present invention, the extract is subject to a step of copolymerization with acrylic resins, where the acrylic resin may be derived from acrylic acid or from metacrylic acid.

In an alternative variation for carrying out the process for producing a plant extract of Acacia Mimosa, Acacia Negra, modified to acquire the desired astringent characteristics according to the present invention, the extract is subjected to a controlled reaction of copolymerization with acrylic resins that may be derived from copolymerization of acrylic acid with metacrylic acid.

The plant extract of Acacia Mimosa, Acacia Negra, chemically modified and having astringent characteristics, obtained according to the present invention by means of a process involving a specific controlled step of copolymerization with acrylic resins, is used as a tanning agent in the processes of transformation of hides.

The plant extract of Acacia Mimosa, Acacia Negra, chemically modified and having astringent characteristics, obtained according to the present invention may also be used to advantage and adequately as a retanning agent in the process of transformation of chrome-tanned leathers.

The new plant extract of Acacia Mimosa, Acacia Negra, modified and having astringent characteristics according to the present invention, may be used as a retanning agent in the process of transformation of tanned leathers, mixed to other plant extracts that may be in natura or may also have been modified by means of any other processes already known in the art.

The new plant extract of Acacia Mimosa, Acacia Negra, modified and having astringent characteristics according to the present invention, may also be used for retanning and transformation of chrome-tanned leathers that may have been subjected to a hydrofuging process, and also in the processes of transformation of leathers that have been tanned using aldehydes.

As a result of the modifications proposed in the present invention, and according to the operating variations pointed out above and the purposes to be fulfilled, there is obtained a highly astringent product, copolymerized with acrylic resin that maintains the desired characteristics of the extract of Acacia Mimosa in addition to other desired characteristics.

The new extract of Acacia Mimosa, modified according to the process of the present invention, was subjected to physical and chemical analyses, the results of which are shown in Table I below in comparison with a commercial extract of Acacia Mimosa.

TABLE I

TYPICAL ANALYSIS

| | Commercial Extract of *Acacia Mimosa* | Modified Extract of *Acacia Mimosa* according to the present invention |
|---|---|---|
| Taning Agent (%) | 72.0 | 74 to 82 |
| Non-Tanning Matter (%) | 21.0 | 10 to 15 |
| Non-Soluble Matter (%) | 1.0 | 0 to 2.5 |
| Humidity (%) | 6.0 | 5.0 to 7.0 |
| pH | 4.5–5.0 | 4.0 to 5.0 |
| Acids (meq $H^+$) | 16.9 | 10 to 70 |
| Salts | 65.9 | 35 to 90 |
| Astringency | 3.6 | 4.0 to 8.0 |

Practice of the Present Invention

The present invention is illustrated by means of the following examples, which should not be construed as limitative to the scope of the invention, there also being incorporate therein other variants hereof.

EXAMPLE 1

There is used a vessel of stainless steel or carbon steel coated with glass, with a capacity of 8,000 liters, provided with a cooling system and also a heating system by means of a steam coil or a jacket, and the conditions required to achieve a pressure of 9 kgf/$cm^2$.

The process is developed in two steps, in the first step there is prepared the acrylic resin and in the second step there is carried out the copolymerization with the tannin.

In the step of preparation of the acrylic resin, there are used condensers to condense the gasses and an entirely open cooling system.

Thereafter, water is added in an amount between 220 kg and 552 kg, preferably 400 kg, while stirring the mixture, and there is added an amount between 96 kg and 240 kg of glacial acrylic acid, preferably in an amount of 174 kg.

Thereafter, there is slowly added to the mixture an amount between 38.4 kg and 96 kg of thioglycolic acid, preferably in an amount of 70 kg, or another catalyst capable of inducing the formation of free radicals.

In this step, there occurs an exothermal reaction, and the temperature reaches 95° C., thus the vessel should be subject to cooling. The mixture is left to cool until reaching a temperature of 30° C.

There is performed an adjustment of the pH value, using an alkali, a solution of sodium hydroxide, ammonium hydroxide, calcium hydroxide, potassium hydroxide, or another reagent, until the pH value reaches 6.0.

There is added over the precedent product an amount between 1414 kg and 3536 kg, or ideally 2564 kg of extract of Acacia Mimosa, Acacia Negra, in powdered form, previously dissolved in an amount of water between 1331 liters and 2413 liters, preferably 3328 liters, heated to a temperature between 45° C. and 80° C.; or alternatively there is added over the product an amount between 2745 kg and 6864 kg, preferably an amount of 4977 kg of extract of Acacia Mimosa, Acacia Negra, in liquid form, at a concentration of 50% in solid matter content.

This mixture is heated under vigorous stirring until reaching a temperature between 67 and 98° C., preferably 84° C., for a period of 5 hours.

Still under intense and vigorous stirring, there is slowly added the sodium sulphite or sodium bisulphite, in an amount between 102 kg and 256 kg, preferably in an amount of 186 kg.

The temperature of the mixture is raised, the system being kept heated at a temperature between 45° C. and 127° C., normally at 95° C. The pressure should be comprised between 0.2 kgf/cm$^2$ and 7 kgf/cm$^2$. The reaction time will be 4 hours.

EXAMPLE 2

There is used a vessel of stainless steel or carbon steel coated with glass, with a capacity of 8,000 liters, provided with a cooling system and also a heating system by means of a steam coil or a jacket, and the conditions required to achieve a pressure of 9 kgf/cm$^2$.

The process is developed in two steps, in the first step there is prepared the acrylic resin and in the second step there is carried out the copolymerization with the tannin.

In the step of preparation of the acrylic resin, there are used condensers to condense the gasses and an entirely open cooling system.

Thereafter, water is added in an amount between 220 kg and 552 kg, preferably 400 kg, while stirring the mixture, and there is added an amount between 46 kg and 146 kg of metacrylic acid, preferably in an amount of 93 kg.

Thereafter, there is slowly added to the mixture an amount between 38.4 kg and 96 kg of thioglycolic acid, preferably in an amount of 70 kg, or another catalyst capable of inducing the formation of free radicals.

In this step, there occurs an exothermal reaction, and the temperature reaches 95° C., thus the vessel should be subject to cooling.

The mixture is left to cool until reaching a temperature of 30° C.

There is performed an adjustment of the pH value, using an alkali, a solution of sodium hydroxide, ammonium hydroxide, calcium hydroxide, potassium hydroxide, or another reagent, until the pH value reaches 6.0.

There is added over the precedent product an amount between 1414 kg and 3536 kg, or ideally 2564 kg of extract of Acacia Mimosa, Acacia Negra, in powdered form, previously dissolved in an amount of water between 1331 liters and 2413 liters, preferably 3328 liters, heated to a temperature between 45° C. and 80° C.; or alternatively there is added over the product an amount between 2745 kg and 6864 kg, preferably an amount of 4977 kg of extract of Acacia Mimosa, Acacia Negra, in liquid form, at a concentration of 50% in solid matter content.

This mixture is then heated under vigorous stirring until reaching a temperature between 67 and 98° C., preferably 84° C., for a period of 5 hours.

Still under intense and vigorous stirring, there is slowly added the sodium sulphite or sodium bisulphite, in an amount between 102 kg and 256 kg, preferably in an amount of 186 kg.

The temperature of the mixture is raised, the system being kept heated at a temperature between 45° C. and 127° C., normally at 95° C. The pressure should be comprised between 0.2 kgf/cm$^2$ and 7 kgf/cm$^2$. The reaction time will be 4 hours.

EXAMPLE 3

There is used a vessel of stainless steel or carbon steel coated with glass, with a capacity of 8,000 liters, provided with a cooling system and also a heating system by means of a steam coil or a jacket, and the conditions required to achieve a pressure of 9 kgf/cm$^2$.

The process is developed in two steps, in the first step there is prepared the acrylic resin and in the second step there is carried out the copolymerization with the tannin.

In the step of preparation of the acrylic resin, there are used condensers to condense the gasses and an entirely open cooling system.

Thereafter, water is added in an amount between 32 kg and 96 kg, preferably 400 kg, while stirring the mixture, and there is added an amount between 48 kg and 120 kg of glacial acrylic acid and an amount between 23 kg and 73 kg of metacrylic acid, preferably in amounts of 87 kg and 47 kg, respectively.

Thereafter, there is slowly added to the mixture an amount between 78 kg and 142 kg of thioglycolic acid, preferably in an amount of 117 kg, or another catalyst capable of inducing the formation of free radicals.

In this step, there occurs an exothermal reaction, and the temperature reaches 95° C., thus the vessel should be subject to cooling.

The mixture is left to cool until reaching a temperature of 30° C.

There is performed an adjustment of the pH value, using an alkali, a solution of sodium hydroxide, ammonium hydroxide, calcium hydroxide, potassium hydroxide, or another reagent, until the pH value reaches 6.0.

There is added over the precedent product an amount between 1414 kg and 3536 kg, or ideally 2564 kg of extract of Acacia Mimosa, Acacia Negra, in powdered form, previously dissolved in an amount of water between 1331 liters and 2413 liters, preferably 3328 liters, heated to a temperature between 45° C. and 80° C.; or alternatively there is added over the product an amount between 2745 kg and 6864 kg, preferably an amount of 4977 kg of extract of Acacia Mimosa, Acacia Negra, in liquid form, at a concentration of 50% in solid matter content.

This mixture is then heated under vigorous stirring until reaching a temperature between 67 and 98° C., preferably 84° C., for a period of 5 hours.

Still under intense and vigorous stirring, there is slowly added the sodium sulphite or sodium bisulphite, in an amount between 102 kg and 256 kg, preferably in an amount of 186 kg.

The temperature of the mixture is raised, the system being kept heated at a temperature between 45° C. and 127° C., normally at 95° C. The pressure should be comprised between 0.2 kgf/cm$^2$ and 7 kgf/cm$^2$. The reaction time will be 4 hours.

EXAMPLE 4

There is used a vessel of stainless steel or carbon steel coated with glass, with a capacity of 8,000 liters, provided with a cooling system and also a heating system by means of a steam coil or a jacket, and the conditions required to achieve a pressure of 9 kgf/cm$^2$.

The process is developed in two steps, in the first step there is prepared the acrylic resin and in the second step there is carried out the copolymerization with the tannin.

In the step of preparation of the acrylic resin, there are used condensers to condense the gasses and an entirely open cooling system.

Thereafter, water is added in an amount between 220 kg and 552 kg, preferably. 400 kg, while stirring the mixture, and thereafter there is added an amount between 46 kg and 146 kg of metacrylic acid, preferably in an amount of 93 kg.

Thereafter, there is slowly added to the mixture an amount between 38.4 kg and 96 kg of thioglycolic acid, preferably in an amount of 70 kg, or another catalyst capable of inducing the formation of free radicals.

In this step, there occurs an exothermal reaction, and the temperature reaches 95° C., thus the vessel should be subject to cooling.

The mixture is left to cool until reaching a temperature of 30° C.

There is performed an adjustment of the pH value, using an alkali, a solution of sodium hydroxide, ammonium hydroxide, calcium hydroxide, potassium hydroxide, or another reagent, until the pH value reaches 6.0.

There is added over the precedent product an amount between 1414 kg and 3536 kg, or ideally 2564 kg of extract of Acacia Mimosa, Acacia Negra, in powdered form, previously dissolved in an amount of water between 1331 liters and 2413 liters, preferably 3328 liters, heated to a temperature between 45° C. and 80° C.; or alternatively there is added over the product an amount between 2745 kg and 6864 kg, preferably an amount of 4977 kg of extract of Acacia Mimosa, Acacia Negra, in liquid form, at a concentration of 50% in solid matter content.

This mixture is then heated under vigorous stirring until reaching a temperature between 67 and 98° C., preferably 84° C., for a period of 5 hours.

Still under intense and vigorous stirring, there is slowly added the sodium hydrosulphite, in an amount between 80 kg and 203 kg, preferably in an amount of 146 kg.

The temperature of the mixture is raised, the system being kept heated at a temperature between 45° C. and 127° C., normally at 95° C. The pressure should be comprised between 0.2 kgf/cm$^2$ and 7 kgf/cm$^2$. The reaction time will be 4 hours.

The modified extracts obtained in the experiments described in Examples 1 to 4 exhibited a high tanning agent content, an anionic powder, of light maroon color, hygroscopic, devoid of dust. The physical and chemical characteristics of those new extracts are described below:

| | | Modified Extract of *Acacia Mimosa* according to the present invention |
|---|---|---|
| Tanning Agent (%) | | 74 to 82 |
| Non-Tanning Matter (%) | | 10 to 15 |
| Non-Soluble Matter (%) | | 0 to 2.5 |
| Humidity (%) | | 5.0 to 7.0 |
| pH | | 4.0 to 5.0 |
| Acids (meq $H^+$) | | 10 to 70 |
| Salts | | 35 to 90 |
| Color** | Red | 2.3–2.7 |
| | Yellow | 4.5–6.5 |
| Astringency | | 4.0 to 8.0 |

What is claimed is:

1. A process for obtaining a plant extract containing condensed tannins, with astringent characteristics, modified by copolymerization, to be used in tannage and retanning of skins, comprising:

(a) adding water to a reactor at between 2.0 and 5.8%, by weight, to the total desired weight of a load;

(b) adding to the reactor an amount between 1.2 and 2.5%, by weight, of a copolymerization agent to form a reaction mixture, selected from the group consisting of acrylic acid, methacrylic acid, mixtures of acrylic acid and methacrylic acid and esters thereof; all the while stirring the reaction mixture;

(c) adding thioglycolic acid at between 0.1 and 1.7%, by weight, while cooling the reaction mixture, allowing the same to react whereupon there occurs an exothermal reaction and a temperature reaches 95° C., and after the reaction a product obtained from the reaction being left to cool;

(d) adjusting the pH to values in the range between 3.5 and 7.0, by adding an alkali to the reaction mixture;

(e) either mixing a powdered extract of a plant with water at an amount about 0.5 to 2.0 kg per liter of water; or mixing a solution of tannin in liquid form in a concentration of 25% to 60%;

(f) raising the temperature of the mixture to a range between 67 and 98° C., to carry out the reaction, for a period of 2 to 7 hours (g) adding sodium bisulphite at 0.5 to 4.0%, by weight, of the amount of tannin;

(h) raising the temperature of the reaction mixture, keeping the reaction system heated at a temperature between 45 and 127° C., the pressure being between 0.2 and 7 kgf/cm$^2$; and (i) allowing a reaction time of about 4 hours.

2. The process according to claim 1, wherein in step (a), there is added water at 3.7% by weight.

3. The process according to claim 1, wherein in step (b), there is added an amount of 1.6%, by weight, of said copolymerization agent.

4. The process according to claim 1, wherein said copolymerization agent is glacial acrylic acid.

5. The process according to claim 1, wherein in step (c), there is added thioglycolic acid at 0.6% by weight.

6. The process according to claim 1, wherein in step (d), the pH is adjusted until reaching a value of 6.0 with the addition of an alkali.

7. The process according to claim 1, wherein in step (e) the amount of powdered extract to water is between 1.0 and 1.5 kg per liter of water.

8. The process according to claim 7, wherein said amount of powdered extract to water is between 1.05 and 1.06 kg per liter of water.

9. The process according to claim 1, wherein said solution of tannin in liquid form is at a concentration in the range between 45% and 55% of total solids content.

10. The process according to claim 1, wherein said solution of tannin in liquid form is at a concentration of 50% of total solids content.

11. The process according to claim 1, wherein in step (f) the temperature is 84° C.

12. The process according to claim 1, wherein in step (g), the content of sodium bisulphate is 1.8 by weight relative to the amount of tannin.

13. The process according to claim 1, wherein in step (h) the temperature is raised until reaching 95° C.

14. The process according to claim 1, wherein said modified extract has enhanced astringent characteristics with acid rates in the range of 10 to 70 meq $H^+$.

15. The process according to claim 1, wherein the plant extract contains catecholic tannins or phlobatannins.

16. The process according to claim 1, wherein said plant extract is derived from Acacia Mimosa.

17. A plant extract containing condensed tannins and derived exclusively from Acacia Mimosa, as obtained by the process defined in claim 1, having astringent characteristics, modified by copolymerization, having the following characteristics:

| | |
|---|---|
| % of tanning agents: | 74 to 82 |
| % of non-tanning matter: | 10 to 15 |
| % of non-soluble matter: | 0 to 2.5 |
| % of humidity: | 5.0 to 7.0% |
| pH: | 4.0 to 5.0 |
| Acids (meq $H^+$): | 10 to 70 |
| Salts: | 35 to 90 |
| Astringency: | 4.0 to 8.0. |

18. The modified plant extract according to claim 17, wherein said modified plant extract has the following characteristics:

| | |
|---|---|
| % of tanning agents: | 78.0 |
| % of non-tanning matter: | 13.9 |
| % of non-soluble matter: | 2.1 |
| % of humidity: | 6.0 |
| pH: | 4.4 |
| Acids (meq $H^+$): | 45.4 |
| Salts: | 54.3 |
| Astringency: | 5.6. |

19. The modified plant extract according to claim 17, wherein the condensed tannins are catecholic type tannins or phlobatannins.

20. A process for tanning, comprising: treating skins or hides with a modified plant extract containing condensed tannins and obtained exclusively from Acacia Mimosa, as defined in claim 17.

21. The process according to claim 20, wherein said modified plant extract is derived from the extract of Acacia Mimosa obtained from reforesting.

22. The process according to claim 1, wherein the step (f) is performed for 5 hours.

* * * * *

UNITED STATES PATENT AND TRADEMARK OFFICE

CERTIFICATE OF CORRECTION

PATENT NO. : 6,955,826 B2
APPLICATION NO. : 10/446109
DATED : October 18, 2005
INVENTOR(S) : Luiz H. Lamb et al.

It is certified that error appears in the above-identified patent and that said Letters Patent is hereby corrected as shown below:

In the title page of the Patent (field 54):

At page 1. line 6, “retaining” should read --retanning--

Ar page 1, line 11, “tannings” should read --tannins--

In the Specification:

Column 1, line 6, “retaining” should read --retanning--

Column 1, line 11, “tannings” should read --tannins--

Signed and Sealed this

Twenty-second Day of August, 2006

JON W. DUDAS

*Director of the United States Patent and Trademark Office*